(12) United States Patent
Matsumura et al.

(10) Patent No.: US 8,118,746 B2
(45) Date of Patent: Feb. 21, 2012

(54) ULTRASONIC DIAGNOSTIC APPARATUS

(75) Inventors: Takeshi Matsumura, Chiba (JP);
Ryuichi Shinomura, Saitama (JP);
Tsuyoshi Mitake, Chiba (JP); Mitsuhiro Oshiki, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 1017 days.

(21) Appl. No.: 10/571,578

(22) PCT Filed: Sep. 9, 2004

(86) PCT No.: PCT/JP2004/013140
§ 371 (c)(1),
(2), (4) Date: Nov. 9, 2006

(87) PCT Pub. No.: WO2005/025425
PCT Pub. Date: Mar. 24, 2005

(65) Prior Publication Data
US 2007/0112267 A1 May 17, 2007

(30) Foreign Application Priority Data

Sep. 12, 2003 (JP) ................................ 2003-322070
Mar. 10, 2004 (JP) ................................ 2004-067983

(51) Int. Cl.
*A61B 8/00* (2006.01)
(52) U.S. Cl. ...................................................... 600/443
(58) Field of Classification Search .................... 600/437
See application file for complete search history.

(56) References Cited

U.S. PATENT DOCUMENTS

| 2001/0014774 | A1* | 8/2001 | Grunwald | 600/437 |
|---|---|---|---|---|
| 2004/0133100 | A1* | 7/2004 | Naghavi et al. | 600/425 |
| 2004/0161224 | A1* | 8/2004 | Yamazoe et al. | 386/52 |
| 2004/0234113 | A1* | 11/2004 | Miga | 382/128 |
| 2005/0090742 | A1* | 4/2005 | Mine et al. | 600/443 |
| 2005/0119568 | A1* | 6/2005 | Salcudean et al. | 600/437 |
| 2006/0052702 | A1* | 3/2006 | Matsumura et al. | 600/443 |
| 2006/0173309 | A1* | 8/2006 | Suzuki et al. | 600/437 |

FOREIGN PATENT DOCUMENTS

JP      2000-60853      2/2000

OTHER PUBLICATIONS

Kanai Hiroshi et al. Imaging of Elasticity Distribution in Arterial Wall by Transcutaneous Ultrasound and Electronic Staining.*

(Continued)

*Primary Examiner* — Tse Chen
*Assistant Examiner* — Hien Nguyen
(74) *Attorney, Agent, or Firm* — Cooper & Dunham LLP

(57) ABSTRACT

An ultrasonic diagnostic apparatus for recognition helpful to diagnosis by giving and displaying a score serving as an index of diagnosis.

An ultrasonic diagnostic apparatus comprises a displacement measuring section (109) for measuring the displacement of an organism tissue of a subject (100) according to a reflection echo signal received correspondingly when an ultrasonic wave is transmitted from a probe (101) to the subject (100), an elastic image creating section for creating an elastic image after determining the distortion amount or the elastic modulus from the displacement, and an image display (107) for displaying the elastic image.

The ultrasonic diagnostic apparatus further comprises scoring means for specifying the distorted state or elastic state according to the information on the elastic image outputted from the elastic image creating section.

20 Claims, 12 Drawing Sheets

OTHER PUBLICATIONS

Kanai et al., Imaging of Elasticity Distribution in Arterial Wall by Transcutaneous Ultrasound and Electronic Staining, Aug. 2003, vol. 51, No. 8, pp. 805-812.*

International Search Report in International application No. PCT/JP2004/013140.

Feb. 10, 2010 European official action in connection with counterpart European patent application No. 04 787 803.8.

Wen-Chun Yen et al., "Elastic Modulus Measurements Of Human Liver and Correlation With Pathology", Ultrasound in Medicine and Biology, New York, NY, US, vol. 28, No. 4, Apr. 1, 2002, pp. 467-474, XP004361097 ISSN: 0301-5629.

Tsuyoshi Shiina et al., "Real Time Tissue Elasticity Imaging Using the Combined Autocorrelation Method", Journal of Medical Ultrasonics, Japan Society of Ultrasonics in Medicine, Tokyo, Japan, vol. 29, Autumn, Sep. 21, 2002, pp. 119-128, XP008033652 ISSN: 1346-4523.

Jul. 28, 2010 Japanese official action in connection with counterpart Japanese patent application.

Wen-Chun Yeh et al. (2002), "Elastic Modulus Measurements of Human Liver AndCorrelation With Pathology", Ultrasound in Medicine and Biology, New York, NY, US, vol. 28, No. 4, pp. 467-474.

Tsuyoshi Shiina et al. (2002), "Real Time Tissue Elasticity Imaging Using the Combined Autocorrelation Method", Journal of Medical Ultrasonics, vol. 29, No. Autumn, pp. 119-128.

T. Matsumura et al. (2004), "Diagnostic Results for Breast Disease by Real-time ElasticityImaging System", 2004 IEEE Ultrasonics Symposium, Aug. 23-27, 2004, IEEE vol. 2, pp. 1484-1487.

Ako Itoh et al. (May 2006), "Breast Disease: Clinical Application of US Elastography for Diagnosis", Radiology May 2006, vol. 239, No. 2, pp. 341-350, XP002552069.

Nov. 6, 2009 European Search Report incounterpart European application No. EP 04 78 7803.

* cited by examiner

FIG. 6
(a)
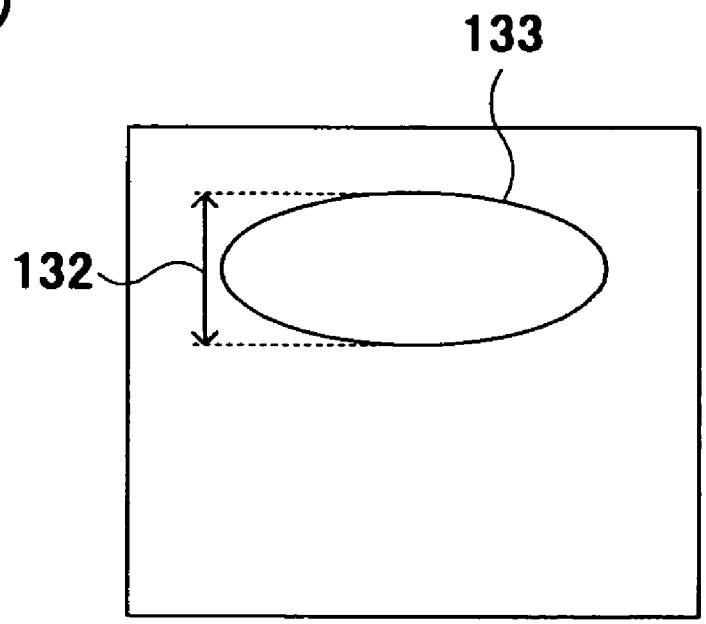
COMPRESSION
(b)
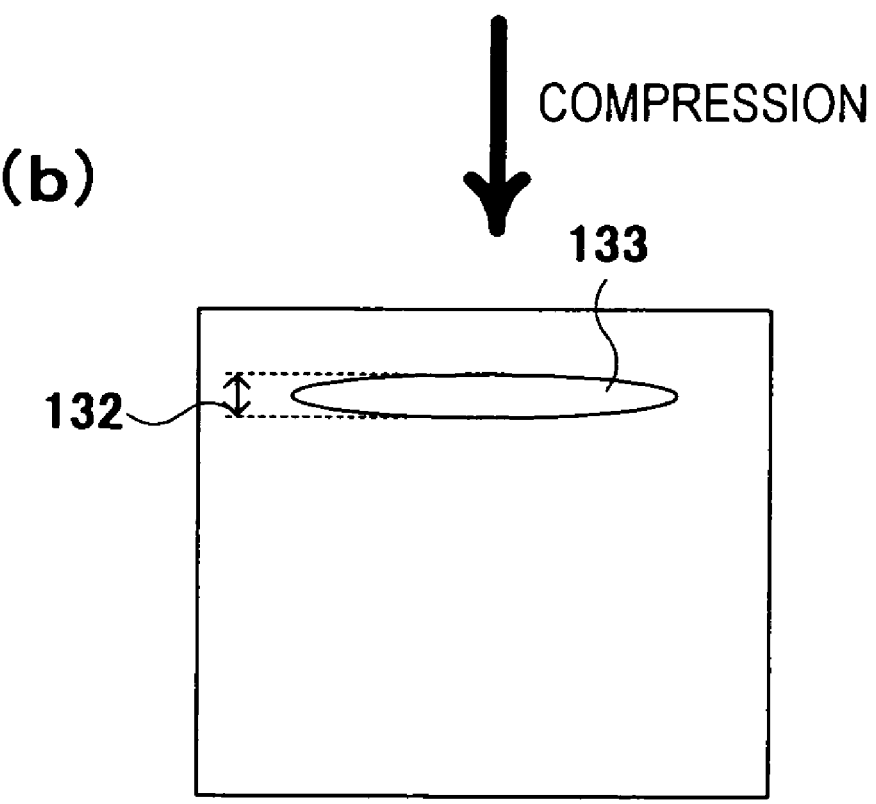

CENTRAL REGION OF INTEREST

A PLURALITY OF REGION OF INTEREST

ULTRASONIC DIAGNOSTIC APPARATUS

TECHNICAL FIELD

The present invention relates to an ultrasound apparatus for displaying hardness and softness of organism tissues as an elastic image using ultrasonic waves with regard to a diagnostic region of an object to be examined.

BACKGROUND ART

A conventional commonly used ultrasound apparatus was composed of: an ultrasound transmission/reception controlling means for controlling the ultrasound transmission/reception; an ultrasound transmission/reception means for transmitting and receiving the ultrasonic waves to/from the object; a tomographic scanning means for obtaining a tomographic image data repeatedly with predetermined cycles in the body of the object including the dynamic tissues from the ultrasound transmission/reception controlling means; and an image display means for displaying the time-series tomographic image data being obtained by the tomographic scanning means.

And the configuration of organism tissues of the object was displayed as, for example, B-mode tomographic image.

Recently, two methods for imaging have been suggested. One method is to apply an external force artificially from the body surface of the object with a pressure device or a probe and compress the internal organism tissues, obtain the displacement in the respective points using the calculation of correlation coefficient of the ultrasound reception signals of adjacent two frames in time series (the two frames that follows in the series), measure the distortion by spatially differentiating the displacement, and construct the images of the distortion data. Another method is to construct the images of the elastic modulus such as Young's modulus of organism tissues from the stress distribution and the distortion data by external force. By the elastic images based on the distortion and/or elastic modulus data (hereinafter referred as elastic frame data), it is possible to measure the hardness or softness of organism tissues and display it as elastic images.

These methods for the ultrasonic diagnostic apparatus are disclosed in Patent Document 1 and Patent Document 2.

Patent Document 1: JP-A-1993-317313
Patent Document 2: JP-A-2000-060853

However, these methods for constructing images of elastic modulus data of organism tissues by conventional ultrasound apparatuses merely recognize the degree of hardness with regard to an actual disease, which does not give an index for diagnosing the disease.

BRIEF SUMMARY

In an aspect of this disclosure, there is provided an ultrasound apparatus that gives a helpful index for diagnosing the disease.

In another aspect of this disclosure, there is provided an ultrasonic diagnostic apparatus that comprises:

a displacement measuring section for transmitting the ultrasonic waves from a probe to an object to be examined, receiving the reflected echo signals corresponding to the transmission of the ultrasonic waves, and measuring the displacement of organism tissues of the object based on the reflected echo signals;

an elastic image constructing section for constructing an elastic image by obtaining the distortion amount or the elastic modulus from the displacement; and a display section for displaying elastic images, wherein the ultrasonic diagnostic apparatus comprises a scoring means for specifying the distorted state or elastic state according to the information on the elastic images being outputted from the elastic image constructing section. This scoring means specifies the distorted or the elastic state according to the size of the area or the formation of the elastic images. Also, the ultrasound apparatus comprises a tomographic image constructing section for constructing the tomographic images from the reflected echo signals, wherein the scoring means specifies the distorted state or elastic state according to the relation with the hard portion region in the elastic images corresponding to the specified regions on the tomography.

Consequently, by giving the scores that correspond with the index of the diagnosis using the elastic images and/or tomographic images, it is possible to provide recognition that contributes to the diagnosis.

BRIEF DESCRIPTION OF THE DRAWINGS

FIG. 6 is a diagram illustrating scoring by variance of region on an elastic image caused by pressure.

BEST MODE FOR CARRYING OUT THE INVENTION

Figure 1:
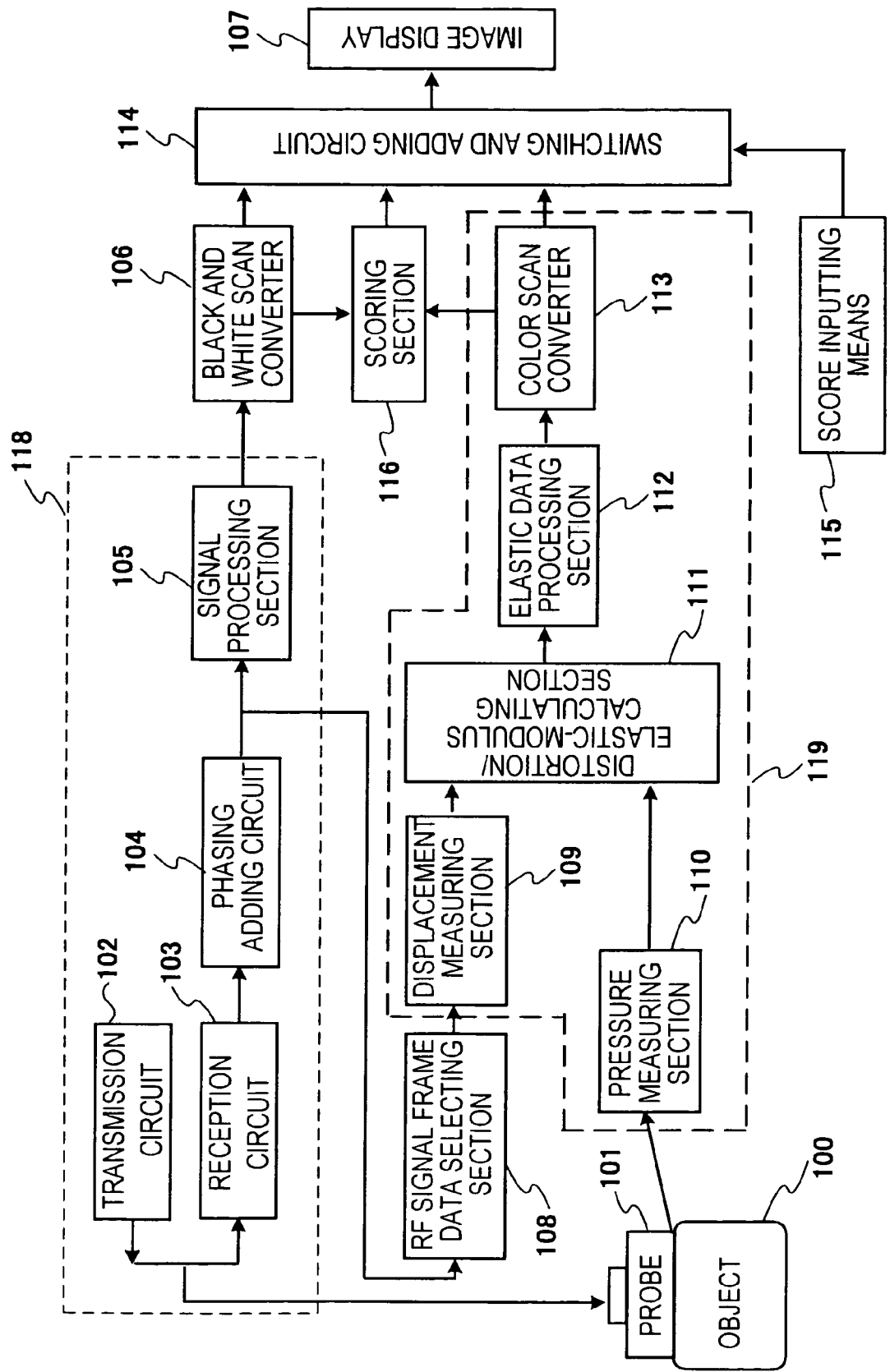
FIG. 1 illustrates a block diagram of an ultrasonic diagnostic apparatus according to an exemplary embodiment of the present disclosure.

Hereinafter the embodiment of the present invention will be described in detail according to the attached drawings. FIG. 1 is a block diagram illustrating the embodiment of the ultrasonic diagnostic apparatus by the present invention. This ultrasonic diagnostic apparatus obtains the tomographic images for a diagnostic region of object to be examined 100 using ultrasonic waves, and displaying elastic images that indicate the hardness or softness of organism tissues.

As illustrated in FIG. 1, this ultrasonic diagnostic apparatus comprises:

tomographic image constructing section 118 for constructing tomographic images using ultrasound probe 101, transmitting circuit 102, receiving circuit 103, phasing adding circuit 104 and signal processing section 105;

elastic image constructing section 119 for constructing elastic images using displacement measuring section 109, pressure measuring section 110, distortion/elastic modulus calculating section 111, elastic data processing section 112, and color scan converter 113. It further comprises black and white scan converter 106 for image converting the outputted signals of the tomographic image constructing section, image display 107, RF frame data selecting section 108, switching and adding circuit 114, score inputting means 115 for inputting the score, and scoring section 116 for specifying the distorted state or elastic state from elastic or tomographic images.

An ultrasound transmitting/receiving means comprises ultrasound probe 101, transmitting circuit 102, receiving circuit 103, phasing adding circuit 104 and signal processing section 105. This ultrasound transmitting/receiving means is for obtaining a tomographic image by making the ultrasound beam scan toward a fixed direction inside the body of Object 100 using ultrasound probe 101. Ultrasound probe 101 is formed by setting a number of transducers in array in strip forms, and is for transmitting and receiving the ultrasonic waves to/from object 100. Though the diagram is omitted, the transducers that are the source of the ultrasonic waves and for receiving the reflected echo is embedded in ultrasound probe 101. The respective transducers are generally configured with two functions. One is to convert inputted wave pulses or transmitting signals of continuous waves into ultrasonic waves and emit those waves. The other is to receive the ultrasonic waves being reflected from inside object 100, convert them into electric receiving signals and output those signals.

Transmitting circuit is for generating the transmitting pulses to irradiate the ultrasonic waves by activating ultrasound probe 101, and for setting the focusing point of the ultrasonic waves being transmitted by embedded transmitting phasing adding circuit to a certain depth. Receiving circuit 103 is for amplifying the reflected echo signals being received by ultrasound probe 101 with predetermined gain. The amplified receiving signals of the same number as the respective transducers are inputted to phasing adding circuit 104 as respective independent receiving signals. Phasing adding circuit 104 is for inputting the receiving signals being amplified by receiving circuit 103, controlling their phase, and forming the ultrasonic beams corresponding to one or plural focusing point. Signal processing section 105 is for inputting the receiving signals from phasing adding circuit 104, and executing a variety of signal processing such as gain compensation, logarithmic compression, edge enhancement and filtering.

Black and white scan converter 106 is for obtaining the RF signal frame data from inside object 100 including the dynamic tissues using the reflected echo signals being outputted from signal processing section 105 of the ultrasound transmitting/receiving means, and making display this RF signal frame data on image display 107 via switching and adding circuit 114. Thus black and white scan converter 106 comprises a tomographic scanning means for reading out the RF signal frame data sequentially with a cycle of a television system and a means for controlling the system, such as, an A/D converter for converting the reflected echo signals from signal processing section 105 into the digital signals, a plurality of frame memory for storing the tomographic data being digitized by the A/D converter, and a controller for controlling these operations.

Image display 107 is for displaying the B-mode tomographic images, i.e. time-series tomographic image data being obtained by black and white scan converter 106, and comprises a D/A converter for converting the image data being outputted from black and white scan converter 106 via switching and adding circuit 114 into the analog signals and a color TV monitor for inputting the analog video signals from this D/A converter and displaying them as images.

In this embodiment, RF signal frame data selecting section 108 and displacement measuring section 109 branching off the output side of phasing adding circuit 104 are set up, and also pressure measuring section 110 is set up parallel to them in the purpose of obtaining the modulus of tissue elasticity. Distortion/elastic modulus calculating section 111, elastic data processing section 112 and color scan converter 113 are set up in the latter part of displacement measuring section 109 and pressure measuring section 110, and switching and adding circuit 114 is set up in the output side of color scan converter 113 and black and white scan converter 106. Then the output power of black and white scan converter 106 and color scan converter 113 is brought in to scoring section 116, and the scoring process is executed there. The details on this scoring process will be described later.

Displacement measuring section 109 is for executing 1-dimensional or 2-dimensional correlation process according to one set of RF signal frame data being selected by RF signal frame data selecting section 108, and for measuring the respective displacement or displacement vector (the direction and the size of the displacement) on the tomographic images. As the detection method for the displacement vector there are, for example, the block matching method and the gradient method that are described in Patent Document 1. The block matching method is for dividing images into blocks consisting of, for example, N×N pixels, extracting the block which is the best approximation to the focused block among the present frames, and executing the predictive coding with reference to the extracted blocks.

Pressure measuring section 110 is for measuring or conjecturing the pressure of inner body of the diagnosis region of object 100. This ultrasonic diagnostic apparatus employs a method for giving the stress distribution to the inner body of the diagnosis region of subject 100, for by pressurizing or depressurizing with a pressurizer (not shown in the diagram) installed in probe head 1011, as transmitting/receiving ultrasonic waves using ultrasound probe 101 installed in probe head 1011 under the control of controlling section 200. In this method, in order to measure the pressure being applied between probe head 1011 and object 100, for example as illustrated in FIG. 2, pressure sensor 1012 for detecting the pressure being applied upon a rod-shaped member is installed on the side of probe head 1011, the pressure between probe head 1011 and object 100 is measured in a given time phase, and the measured pressure value is sent out to distortion/elastic modulus calculating section 111.

Figure 2:
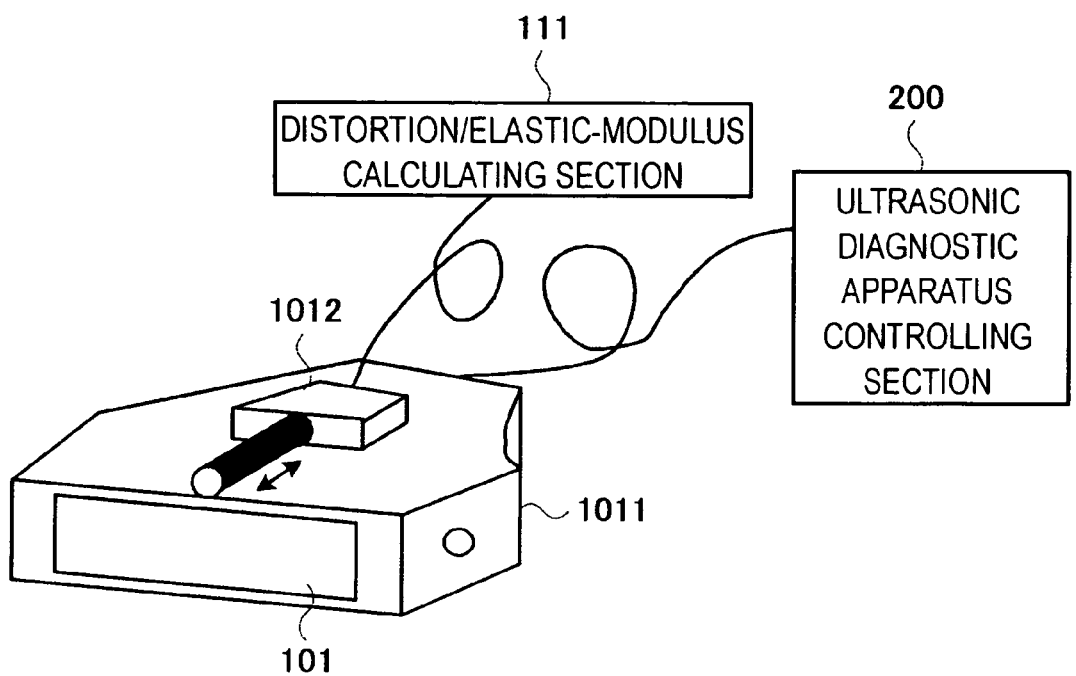
FIG. 2 is a diagram illustrating an example of a method for attaching a pressure measurement unit on an ultrasound probe and for measuring pressure between a head of the probe and a subject.

The pressurizer for pressurizing/depressurizing probe head 1011 is omitted in FIG. 2.

Distortion/elastic modulus calculating section 111 is for calculating the distortion or elastic modulus of the respective points on the tomographic images according to the moving distance (displacement) and the pressure being outputted each from displacement measuring section 109 and pressure measuring section 110, generating the numeric data (elastic frame data) of distortion or elastic modulus, and outputting them to elastic data processing section 112. The calculation of the distortion being performed by distortion/elastic-modulus calculating section 111 is obtained, for example, by the calculation by spatially differentiating the displacement without the pressure data. Also, the calculation of Young's module that is one of the elastic modulus is obtained by calculation with dividing the change of pressure by the change of distance.

Color scan converter 113 comprises the hue information converting means for inputting the elastic frame data being outputted from elastic data processing section 112, the command being outputted from controlling section 200 of the ultrasonic diagnostic apparatus, the upper limit and the lower limit within the configured range among the elastic frame data for the image gradation being outputted from elastic data processing section 112. This means is also for giving the hue information such as red, green and blue as the elastic image data from the elastic frame data. This hue information converting means operates so that the region with a large degree of distortion is converted into red code within the elastic image data, and the region with a small degree of distortion is converted into blue code within the elastic image data. Also, color scan converter 113 can be configured with the above-mentioned black and white scan converter 106. In this case, it can be set so that the region with a large degree of distortion turns brighter in luminance, and the region with a small degree of distortion turns darker within the elastic image data.

Switching and adding circuit 114 is a means to input black and white tomographic data from black and white scan converter 106 and the elastic image data in color from color scan converter 113, and to add or switch over both kinds of images. It is also for outputting only black and white tomographic image data or only elastic image data in color, or for performing the composition of both kinds of images. Also for example, as described in Patent Document 2, black and white tomographic images and the color elastic images or black and white elastic images by black and white scan converter can be displayed simultaneously on one screen of the display. The image data being outputted from switching and adding circuit 114 are to be outputted to image display 107.

Next, the scoring related to the present invention will be described.

Figure 3:
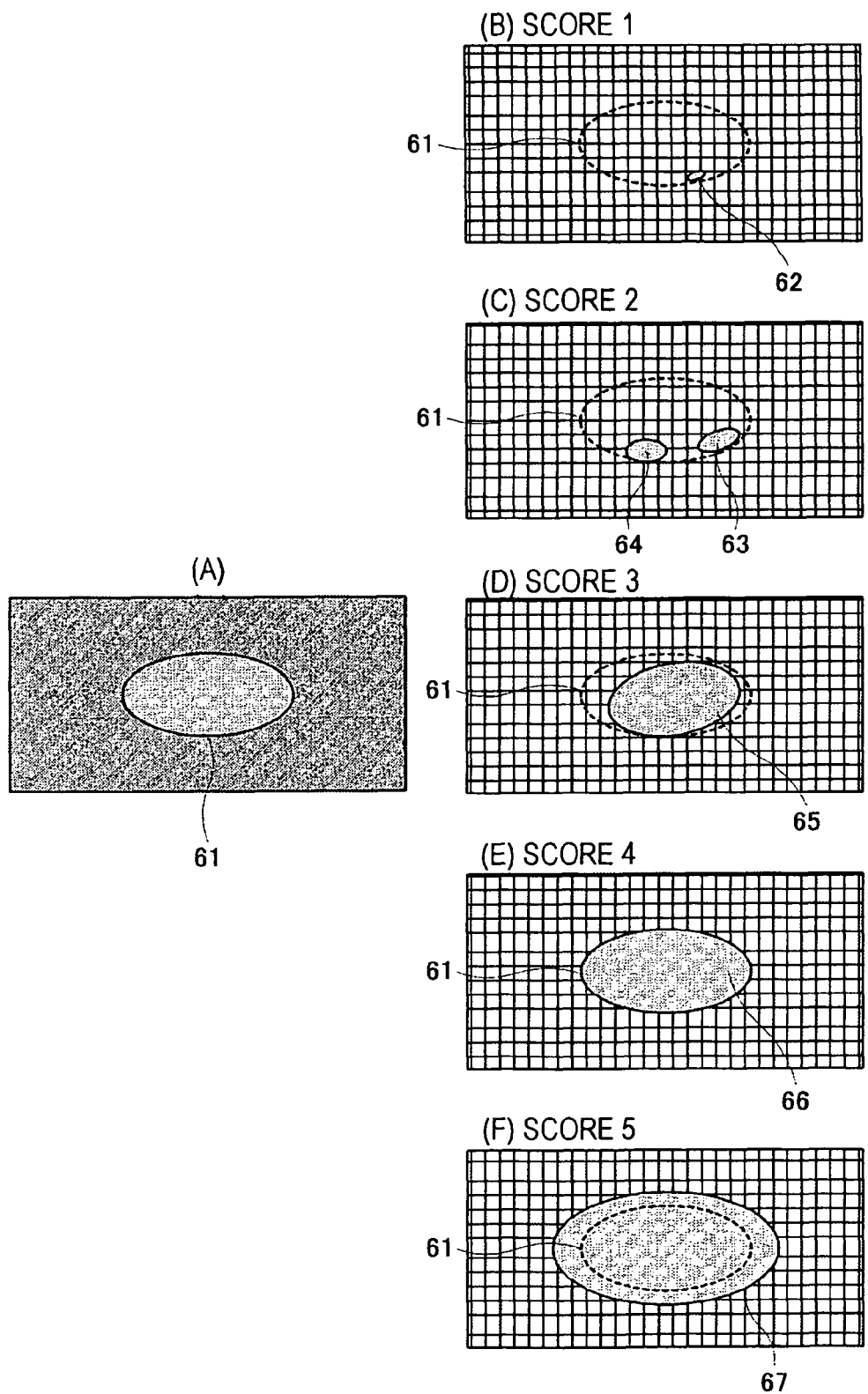
FIG. 3 is a diagram illustrating an example of a scoring process carried out by a score inputting means in the ultrasonic diagnostic apparatus of FIG. 1.

FIG. 3 is a diagram illustrating the first embodiment of the scoring process executed by scoring section 116 in FIG. 1, and FIG. 3(A) is a diagram illustrating an example of black and white tomographic image data (B-mode tomographic image) being outputted from black and white scan converter 106. FIG. 3(B)~(F) are the pattern diagrams illustrating an example of the elastic image data in color being outputted from color scan converter 113, in the case with different symptoms. These elastic image data are actually for color displaying according to their hardness. For example, the soft portion (heavily distorted portion) is displayed in red, while the hard portion (lightly distorted portion) is displayed in blue, and the middle of both in green as a continual color variation. Meanwhile, since color-display is not possible in FIG. 3, a shading method is used instead. The soft region is shaded with rough dots and the hard region with fine dots. In the case of B-mode tomographic image in FIG. 3(A), an oval region 61 in the center is a diseased region such as a tumor of the breast, and is called "low echo region". Also, the regions corresponding to the same coordinate region of the low echo region in the elastic images are displayed in oval shapes with dotted line in FIG. 3(B)~(F). According to the condition of in which the elastic image data are displayed, the elastic images are classified into score 1~score 5 by executing the scoring process with the operation of score inputting means 115 of the elastic image data. The respective scores 1~5 have the following criteria, and the scoring process is executed by the observer determining whether these criteria are met by the image. Hereinafter the respective criteria 1~5 will be described.

Score 1: The case, as illustrated in FIG. 3(B) that hard region 62 by the elastic image is not recognized clearly inside of low echo region 61.

Score 2: The case, as illustrated in FIG. 3(C) that hard regions 63 and 64 by the elastic images are partially recognized, avoiding the center region of low echo region 61.

Score 3: The case, as illustrated in FIG. 3(D) that hard region 65 is recognized including the center region of low echo region 61, though not reaching the circumference (border).

Score 4: The case, as illustrated in FIG. 3(E) that hard region 66 is evenly distributed, reaching the circumference (border) of the low echo region 61.

Score 5: The case, as illustrated in FIG. 3(F) that hard region 67 is covering the whole area of low echo region 61, running off the circumference (border) of low echo region 61.

The hard region here, as the distorted image of the elastic images, can be distinguished as a region that measured a smaller distortion than threshold Ts of a distortion. For example, when 0% of distortion is set as threshold Ts, the hard region is distinguished as a region (measure point group) that did not receive any compression even with pressure from the body surface. In the case of using the elastic modulus images as the elastic image by taking in the suppressed strength upon scanning the diagnosis region, the region that has bigger elastic modulus than threshold Ty of an elastic modulus may be distinguished as the hard region.

Figure 4:
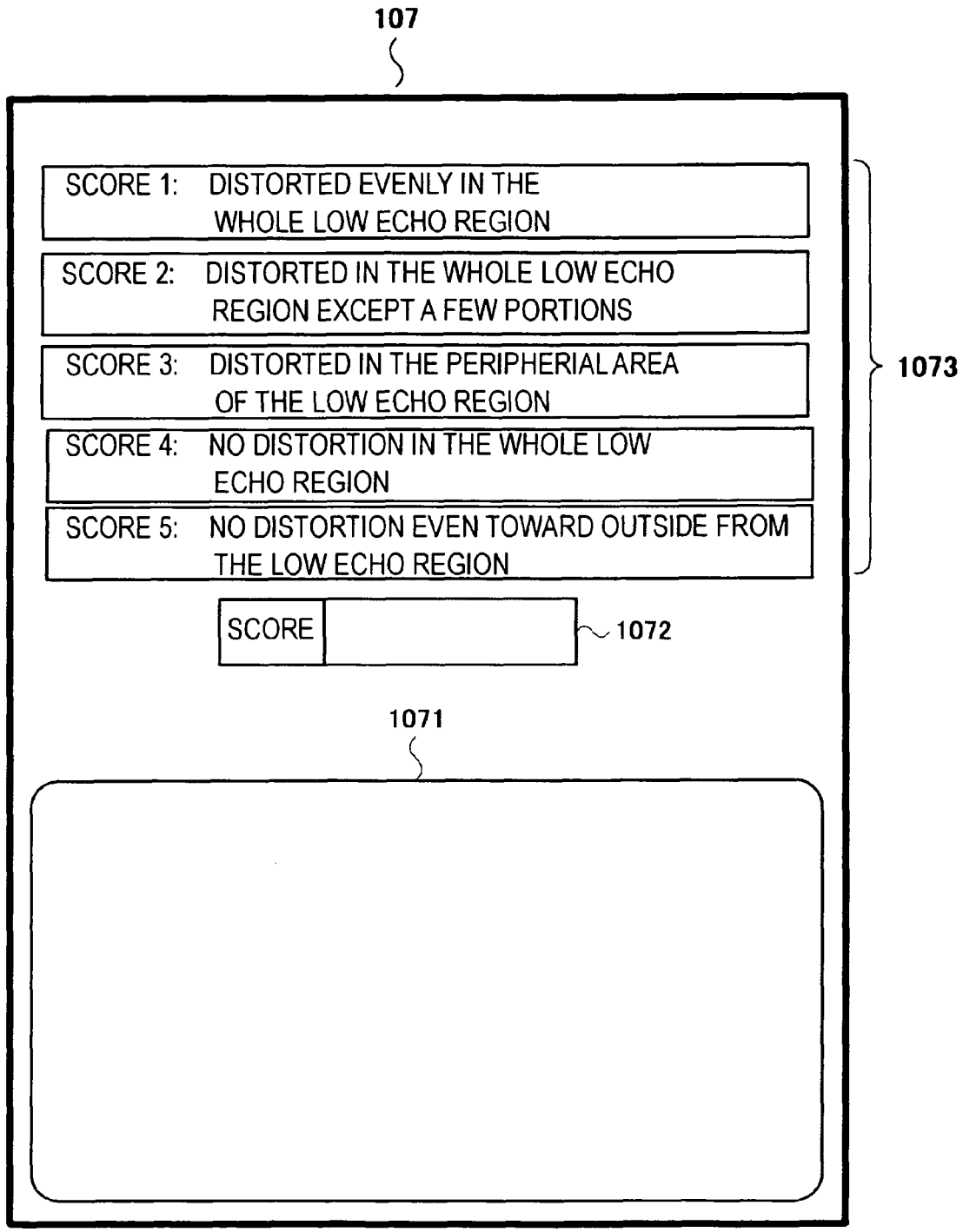
FIG. 4 is a diagram illustrating an example of an image indicator display in a case of implementing the scoring process of FIG. 3.

By the above-mentioned scoring (classification), it is possible to give an indicator as well as assistance for diagnosing an illness. FIG. 4 is a diagram illustrating a display example of image display 107 for the case of executing the scoring process using score inputting means 115. The superposed translucence color images of the elastic image data indicating the distribution of hardness of the tissues on the B-mode tomographic images such as (B)~(F) of FIG. 3 are displayed on display screen 1071 of image display 107, and column 1072 for inputting the scoring index and display region 1073 for displaying the index of the respective scores are set up on the right to the display screen. This display region 1073 is for displaying the brief description of the content of the above-mentioned respective scores, and for displaying diagrams such as (B)~(F) in FIG. 3 in conjunction with those descriptions. The examiner inputs the score as he/she thinks is appropriate to scoring index inputting column 1072, as looking at display indicator 1071 and comparing the images with scoring index 1073. The above-mentioned operations are executed by score inputting means 115. Additionally, the images being displayed on display screen 1071 may be arranged so that the B-mode tomographic images are displayed on a separate window as illustrated in FIG. 3(A). This makes it possible to improve the visibility during the scoring process. The scores being inputted to score index inputting column 1072 may also be set to be linked to the reporting function of each patient being installed in the ultrasonic diagnostic apparatus, and to be inputted also to the scoring index inputting column being provided in the reporting function at the same time. It also may be arranged so that the model diagrams to be the index for the scoring such as (B)~(F) of FIG. 3 are included in display region 1073.

Described in the above embodiment was the scoring process being implemented by the examiner as looking at the images on display screen 1071, but scoring section 116 automatically executes scoring (classification) using image processing. Hereinafter the automatic scoring process by this scoring section 116 will be described. Scoring section 116 is for executing the edge detection that detects with well known edge detection software with regard to color elastic image data (distorted images) being outputted from color scan converter 113, and for obtaining area B of hard-portion regions 62~67 with such as the number of pixels.

In the second embodiment, the scoring with only elastic image data will be illustrated. For example, the elastic images to be the reference images for the reference information are obtained in advance, and the scores according to the size of the area of the elastic images are set as below, representing the number of pixels of the region on the elastic images as B:

If X1<B Score 1
If X2<B≦X1 Score 2
If X3<B≦X2 Score 3
If X4<B≦X3 Score 4
If B<X4 Score 5

And the scoring is to be performed by applying the size of the area of the newly obtained elastic data to area B being set as the above. Also, the scores may be set according to the form of the elastic images by setting the elastic images that are connected in sequence as above score 2, or the elastic images that are connected with a smooth circular form as above score 3.

Figure 5:
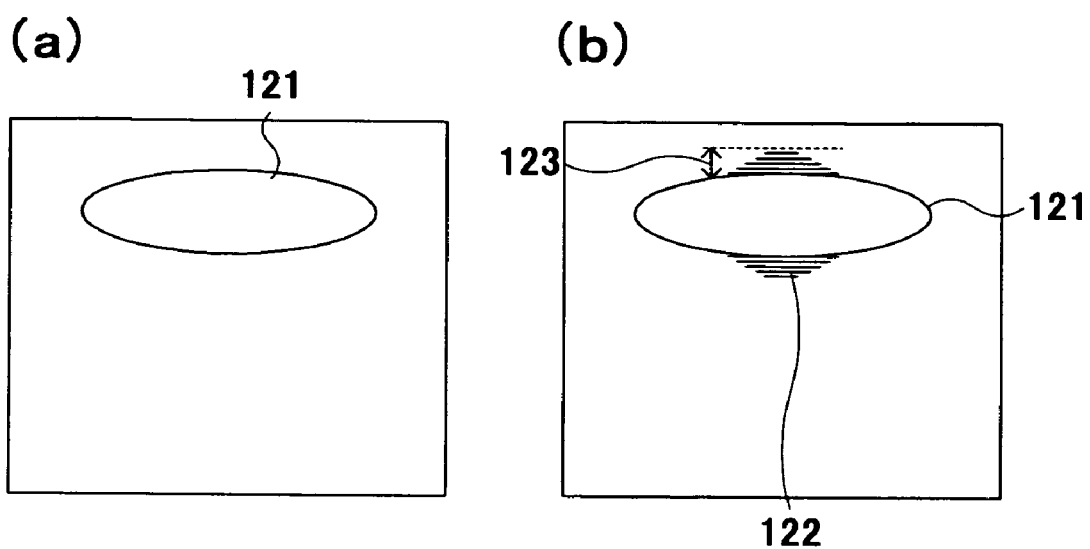
FIG. 5 is a diagram illustrating scoring by stress signals.

The scoring process using the characteristic feature that the stress signals are put out on the elastic images when exerting pressure on the subject is illustrated in FIG. 5. FIG. 5(*a*) and (*b*) are the diagrams illustrating the state of subject 100 being pressed by probe 101. When exerting pressure on a malignant tumor, stress signal 122 is displayed as shown in FIG. 5(*b*). FIG. 5(*a*) is illustrating a benign tumor.

In scoring section 166, the score corresponding with width 123 of stress signals 122 is set in advance. The scores are set, for example, so that the bigger the width the elastic images indicate a malignant tumor as illustrated in FIG. 4. And the scoring for elastic image 121 is executed by comparing the width being set corresponding to the score with width 123 of stress signals 122 on obtained elastic image 121. Though an example of implementing the scoring using the width of stress 122 here, it also can be implemented using the dimension of stress signals 122. In this way the scoring can be performed by the stress signals of the elastic images.

Also, an example of executing the scoring process using the elastic images being varied by exerting pressure on the object is illustrated in FIG. 6. In the case that the tumor of the image is malignant, there is a feature that when gradual pressure is exerted on the subject, the region displayed in blue for example, gets gradually smaller. On the contrary, when the tumor on the image is benign, there is a feature that causes the blue region to get bigger gradually upon exerting gradual pressure on the object. Given this factor, the scores with regard to the feature corresponding to the color change of the region being generated by the compression in scoring section 116 are set as illustrated in FIG. 4. And the scoring is performed according to colors being varied in accordance with the compression on the elastic images. In this way, it is possible to perform the scoring according to the previously mentioned variance of the region by compression in the elastic images.

Figure 7:
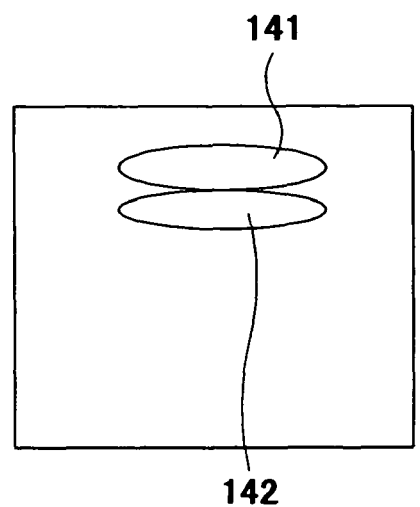
FIG. 7 is a diagram illustrating scoring by hue patterns of the elastic images.

The example for executing the scoring process using a cyst pattern is illustrated in FIG. 7. The cyst pattern is a pattern that indicates shallow depth portion 141 in a particular region of elastic images being displayed in blue, and deep depth portion 142 in red. Experience shows that the regions being displayed using this pattern is a benign tumor. Given this factor, the scoring can be executed by setting the program separately in scoring section 116 so that when the cyst pattern is recognized it indicates that the tumor is malignant. In this way the scoring can also be performed according to the hue pattern of the elastic images.

In the above-mentioned embodiment the case for executing the scoring process using only the elastic image data was explained, but an automatic scoring process by the elastic image data using the tomographic image data as reference information will be described in the third embodiment referring to FIG. 3. First, scoring section 116 detects low echo region 61 in the diseased region on black and white tomographic image data (B-mode tomographic images) being outputted from black and white scan converter 106 using well known edge detecting software. Then area A of detected section 61 is obtained using, for example, the number of pixels. Next, scoring section 116 performs edge detection in the same way also on colored elastic image data (distortion images) being outputted from color scan converter 113, and obtains area B of the hard portion being measured in low echo region 61 of the diseased region using, for example, the number of pixels. In the case that the hard portions are scattered as illustrated in sections 63 and 64, the sum of those area is set as area B.

Scoring section 116 implements the scoring process as follows according to the relation between each obtained areas A and B.

First, B/A is calculated as Z as proportion of the areas A and B. Also, as the following thresholds of the area ratio are set in advance in the ultrasonic diagnostic apparatus:

Threshold of score 1 Th1 (for example, 0.1)
Threshold of score 2 Th2 (for example, 0.3)
Threshold of score 3 Th3 (for example, 0.7)
Threshold of score 4 Th4 (for example, 1.0).

With that, the following determination is to be performed:

If Z<Th1 Score 1
If Th1<Z≦Th2 Score 2
If Th2<Z≦Th3 Score 3
If Th3<Z≦Th4 Score 4
If Th4<Z Score 5

Figure 8:
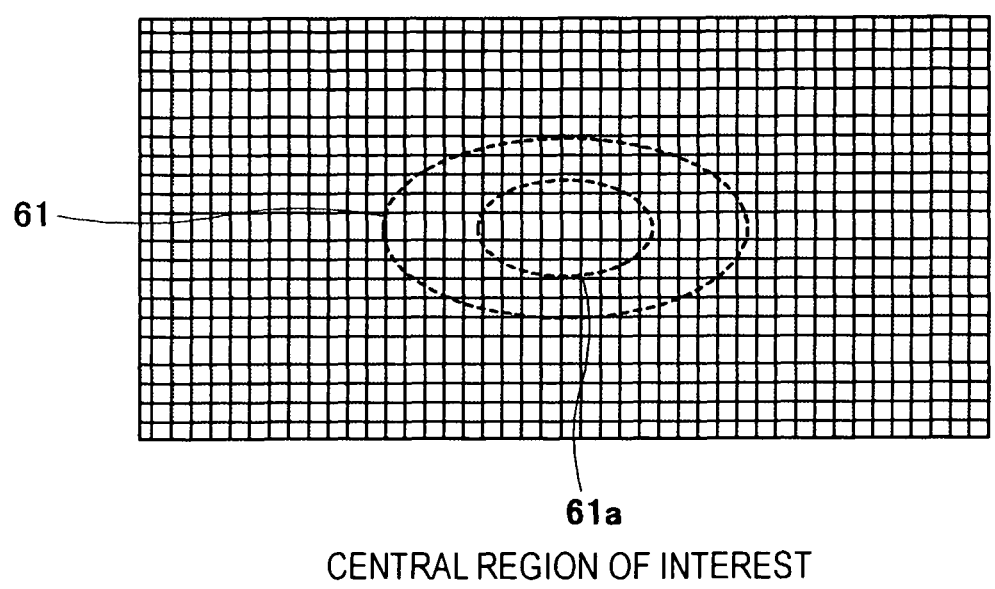
FIG. 8 is a diagram illustrating another embodiment of a scoring process that can be carried out by the score inputting means in the ultrasonic diagnostic apparatus of FIG. 1.

Also, some other options may be added to the above-mentioned scoring method. For example, as illustrated in FIG. 8, region of interest 61*a* in the center of low echo region 61 which has a fixed ratio (for example, area A×0.6) and has a smaller area than the low echo region is set, and a estimation of how much of the hard portion in the elastic image occupies the region of interest 61*a* can be added to the scoring method. By adding this rating, not only the occupied-area ratio of the hard portion corresponding to the low echo region but also how the hard portions are allocated as a spatial distribution are added to the rating of the scoring, and it leads to the result of raising the precision of the estimation.

Figure 9:
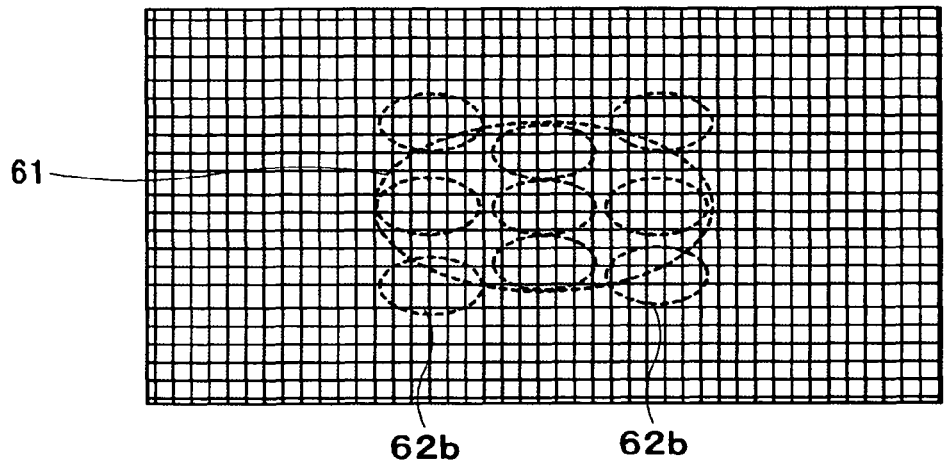
FIG. 9 is a diagram illustrating yet another embodiment of a scoring process that can be carried out by the score inputting means in the ultrasonic diagnostic apparatus of FIG. 1.

Moreover, an estimation of how much the hard portion in the elastic image occupies corresponding not only to the central region of interest but also to a plural interest of regions may be implemented, by setting a border of the low echo region as a reference and setting plural regions of interest 62*b* inside or outside of the border as illustrated in FIG. 9. Also, another option may be used for the estimation of scoring by first rating each plural regions of interest 62*b* if the ratio that the hard portion in the elastic image occupies in each of their area exceed a certain fixed ratio or not, then adding up the regions which exceeded the ratio. Also, the edge detection can be achieved by using methods such as well-known snake method or region growing method. If the edge is hidden by the shadow for example, the methods such as setting ROI or interpolating from surrounding edge information can respond to the problem.

Though an example of the scoring using the occupancy ratio of the hard portion and its ratio being distributed within the low echo region was described in the above-mentioned embodiment, but a scoring can also implemented according to the statistical feature quantity by performing the statistical work with elastic measure point group being included in the low echo region as the (parent of) the population, and the method using its average value will be described below. The total number of the elements of the measure point group that are within the low echo region is set as N, and the distortion or elastic module of the respective measure points is set as $Ei (i=1,2,3 ... N)$ And average value $Em$ of distortion or elastic modulus of the measure point within the low echo region is calculated as below:

$$\text{(Average value } Em) = \Sigma Ei (i=1,2,3, ... N)$$

Also, the threshold values of the average value are set in the ultrasonic diagnostic apparatus in advance as follows:
Threshold value $Tm1$ of score 1
Threshold value $Tm2$ of score 2
Threshold value $Tm3$ of score 3
Threshold value $Tm4$ of score 4.

In the case of calculating the elastic modulus as a value to reflect the elasticity, the scores are set by maintaining the following magnitude relation:

$$Tm1 < Tm2 < Tm3 < Tm4.$$

And the following determination is to be performed:
If $Z < Tm1$ Score 1
If $Th1 < Z \leq Tm2$ Score 2
If $Th2 < Z \leq Tm3$ Score 3
If $Th3 < Z \leq Tm4$ Score 4
If $Th4 < Z$ Score 5

In the case of using the distortion as the value for reflecting the elasticity, the following magnitude relation is set:

$$Tm1 > Tm2 > Tm3 > Tm4$$

And the following determination is to be performed:
If $Tm1 < Z$ Score 1
If $Tm2 < Z \leq Tm1$ Score 2
If $Tm3 < Z \leq Tm2$ Score 3
If $Tm4 < Z \leq Tm3$ Score 4
If $Z < Tm4$ Score 5

The average value was used as an example in the above explanation, but the present invention is not limited to this, and the significance of the scoring method in the present invention is to first execute the statistical work with the measure point group of the elasticity being included in the low echo region as a (parent of) population, and to perform the scoring according to its statistical feature quantity.

A concrete example of an automatic scoring (classification) implemented by scoring section 116 using the image processing will now be described. First, scoring section 116 detects area A of low echo region 61 in the diseased region on the black and white tomographic image data (B-mode tomographic images) being outputted from black and white scan converter 106 as illustrated in FIG. 3, using for example, the region growing method which is a well-known software for region detection. Then it obtains detected area A by using, for example, number of pixels. Next, scoring section 116, in the color elastic image data (distortion images) being outputted from color scan converter 113, counts the number of pixels that are illustrated as hard sections 62~67 within area A. These pixels should have higher luminance value than a predetermined one that the operator of the apparatus can determine in advance. This number of pixels is set as area B. The scoring process below is to be executed according to area A and area B (number of pixels which have higher luminance value than a predetermined luminance value).

First, B/A is calculated as Z, as ratio between areas (number of pixels) A and B. Also, the following thresholds of the area ratio are set in advance in the ultrasonic diagnostic apparatus:
Threshold of score 1 $Th1$ (for example, 0.1)
Threshold of score 2 $Th2$ (for example, 0.3)
Threshold of score 3 $Th3$ (for example, 0.7)
Threshold of score 4 $Th4$ (for example, 1.0)

And now when $Z < 0.7$, the score is executed according to the following rules:
If $Z < Th1$ Score 1
If $Th1 < Z \leq Th2$ Score 2
If $Th2 \leq Z \leq Th3$ Score 3

Further, in the obtained elastic image data (distortion images), if $Th3 \leq Z$ ($0.7 \leq Z$), the sections illustrated as hard sections 65~67 which have higher luminance value than the predetermined one are extracted by well-known applications for region extraction (for example, the region growing method) In this case, the region for the extraction is not limited within low echo region 61, but includes its periphery also as the extracting region.

The extracted area being obtained here is set as C. C/A is calculated as Z', as ratio between area A and area C, and the following determination is to be implemented if the value of Z' is:
$Th3 < Z' \leq Th4$ Score 4
$Th4 < Z'$ Score 5

In the above embodiment, the scoring can be implemented without the region extracting process up to score 3 in the elastic image data.

Figure 10:
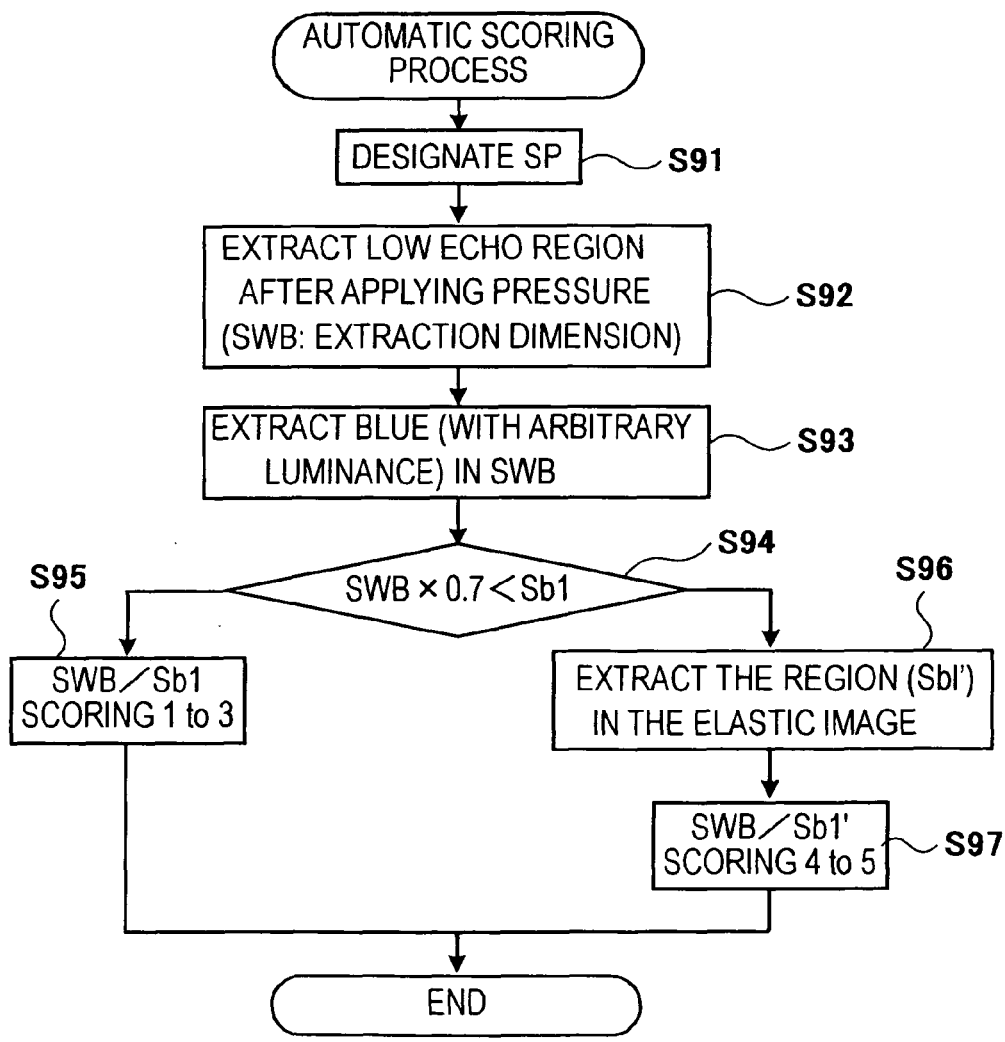
FIG. 10 illustrates a flow chart for an example of an automatic scoring process using a region extracting application.
Figure 11:
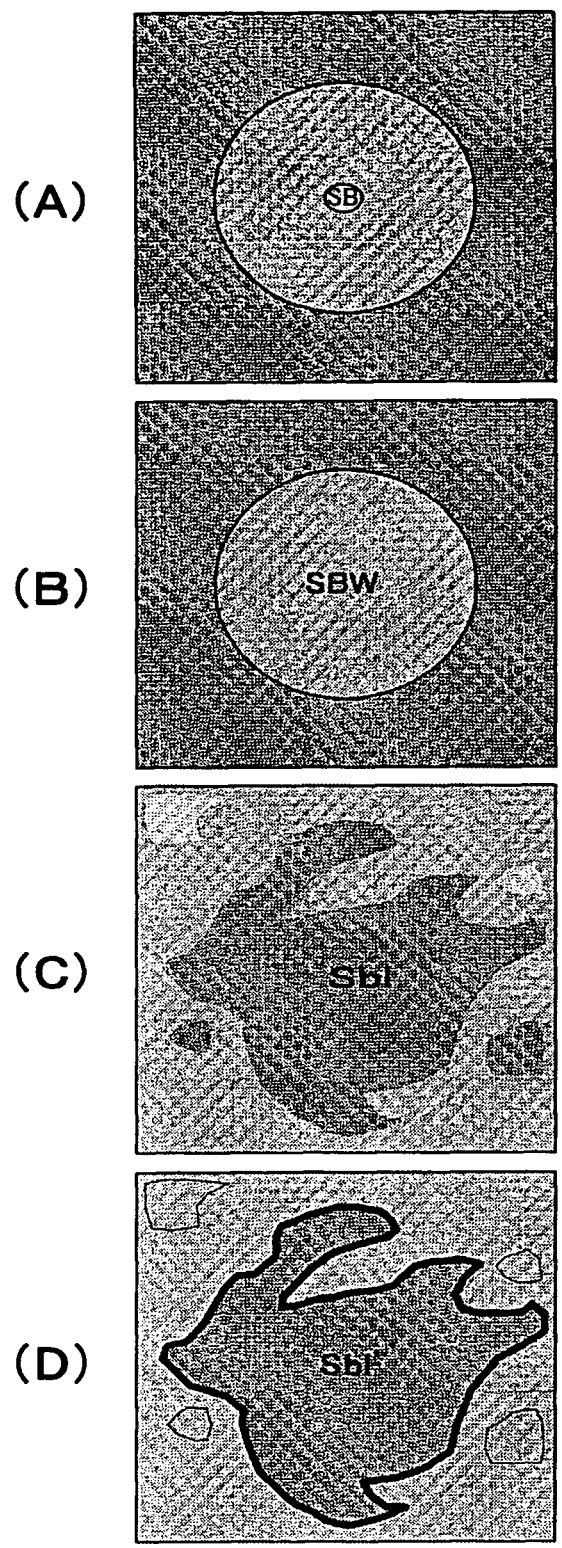
FIG. 11 is a pattern diagram illustrating an example of the operation of the automatic scoring process of FIG. 10.

FIG. 10 is a flow chart illustrating an example of the automatic scoring process using the region extracting application. FIG. 11 is a pattern diagram illustrating an example of the operation for this automatic scoring process. It will be explained here with the region growing method as the region extraction algorithm.

In step S91, the low echo regions that are desirable to be extracted are selected after pressurized by arbitrary means on the displayed B-mode tomographic images, in order to obtain the distortion images. This selection process is executed by designating an arbitrary position within low echo region 61 as a source point (indicated as SP in the diagram) as illustrated in FIG. 11(A).

In step S92, the extraction of low echo region 61 as illustrated in FIG. 11(B) is executed according to source point SP being designated in step S91 and the threshold value given by discretional means. The region growing method is a method for extracting the regions of which the difference of the luminance value is within the value being set in advance (threshold value) in the adjacent region to the designated source point. Consequently, the area of extracted low echo region 61 is calculated by means such as counting the number of pixels. This area is indicated as SBW in FIG. 11(B).

In step S93, the area on the displayed distorted images that have the higher luminance value than the discretionally set luminance value indicating the hard region are counted by the number of pixels. This hard region is indicated as Sb1 in FIG. 11(C).

In step S94, the determination is implemented whether or not area Sb1 of the hard region is smaller than; area SBW of the low echo region×0.7. As a result of the determination, if area Sb1 of the hard region is smaller than area SBW of the low echo region×0.7 (SBW×0.7<Sb1), step S95 is to be carried out. And in step S95, the determined areas will be classified into score 1~3 according to its value.

On the contrary, as a result of the determination, if the area Sb1 of the hard region is bigger than area SBW of the low echo region×0.7 (SBW×0.7≦Sb1), since it may not be within the low echo region, step S96 is to be carried out.

In step S96, the detection of the region (area Sb1') by region growing method on the elastic image data is performed again. In this case the detection is performed up to the region including the peripheral area of the low echo region on the B-mode tomographic images. In this region extracting process, the source point designated on the previous B-mode tomographic images can be used as it is, or the new one may be set additionally. The area of the region being extracted here is set as Sb1'. And in step 97, score 4 and 5 are classified according to the proportion between area SBW of the low echo region and area Sb1' (SBW/Sb1'). To be more precise, if Sb1'<SBW it will be classified as score 4, and if not it will be classified as score 5.

In this way, performing the region extraction by well-known region extracting applications such as the region growing method enables the automatic scoring process according to the hardness distribution of the tissues. Needless to say that the above-mentioned thresholds are mere examples, and they can be varied as the operator desires.

Though the example of detecting the outline information of the low echo region in the diseased region on the B-mode tomographic images using the well-known edge-detecting software was described in the above-mentioned embodiment, another embodiment can be implemented. Another embodiment can be executed by the examiner inputting the outline of the diseased region on the B-mode tomographic images using the interface on the ultrasound apparatus such as mouse or trackball, obtaining area A of section 61 on the basis of the outline information, and executing automatic scoring by comparing with area B being obtained from the above-mentioned method. The above-mentioned scoring is merely an example, and it is essential to perform the scoring using the elastic images that include the distortion images. The above-mentioned numeric values used for scoring are also merely examples, and of course, various sorts of values that are most suitable for each of the actual clinical cases should be applied. Though the scoring method intended particularly for the mammary gland region was described as an example in the above explanation, the scoring method best suited according to each region ought to be defined. Also, the scoring method according to the above-mentioned embodiment can be used not only individually but also by combining a plurality of methods for implementing one scoring process.

In the above embodiment the scoring process by scoring section 116 using black and white tomographic image data (B-mode tomographic data) being outputted from black and white scan converter 106 and color elastic image data (distortion data) being outputted from color scan converter 113 was described, but it can also use the output from signal processing section 105, elastic data processing section 112 or distortion/elastic modulus calculating section 111. Also in the above-mentioned embodiment the pressure measuring section was included in FIG. 1, but the pressure measuring section can be omitted in the case of obtaining the distortion and displaying the distortion image.

Figure 12:
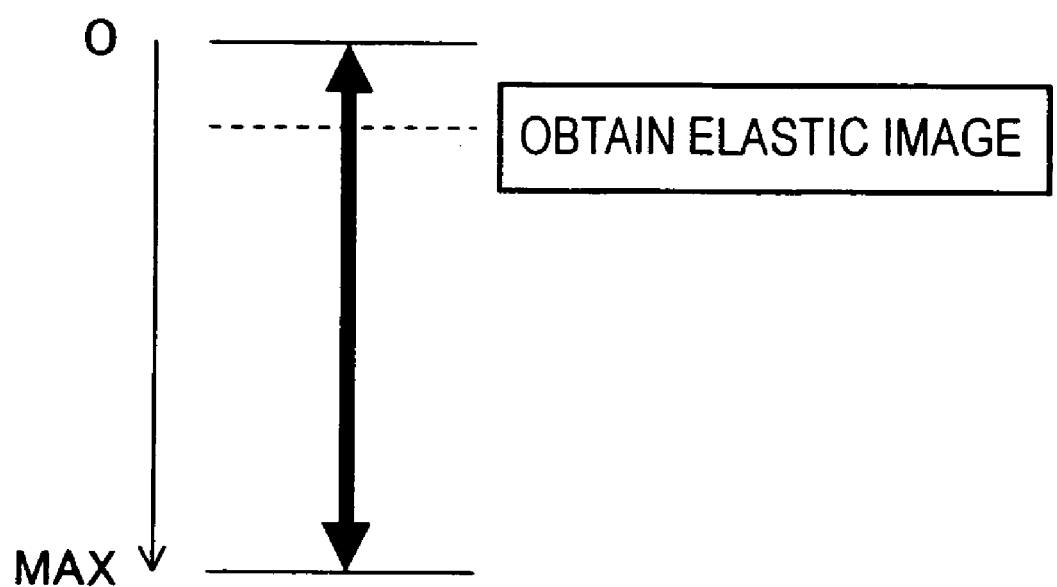
FIG. 12 is a diagram illustrating a timing for obtaining an elastic image for scoring.

FIG. 12 is a diagram illustrating the timing for calculating the distortion or elastic modulus in distortion/elastic-modulus calculating section 111 in the above-described embodiment. In probe 101, the condition of not compressing object 100 is indicated with 0 and the limit of compression is indicated with MAX. The timing for obtaining the elastic images is the timing with lightly compressed condition, so the scoring should be executed corresponding to the obtained elastic images with the condition that have about 3~20% of the limit of compression.

In concrete terms, the pressure value of the limit of compression is detected in advance by pressure sensor 1012, and the obtained pressure value is stored in scoring section 116 as compression MAX value. The pressure value of the elastic images for compressing and obtaining is set using score inputting means 115 referring to the stored compression MAX value. The pressure value for the setting may also be arbitrarily appointed in advance as, for example, 10% of the compression MAX value. By compressing object 100 and obtaining the elastic image at the point of reaching the fixed pressure value, the scoring is to be executed on the obtained elastic image.

Because it is often difficult to distinguish between the hard portion and soft portion of the elastic images in strongly compressed condition, it is possible to improve the accuracy of the scoring by using the elastic image being obtained with the timing of lightly compressed condition as described above.

Figure 13:
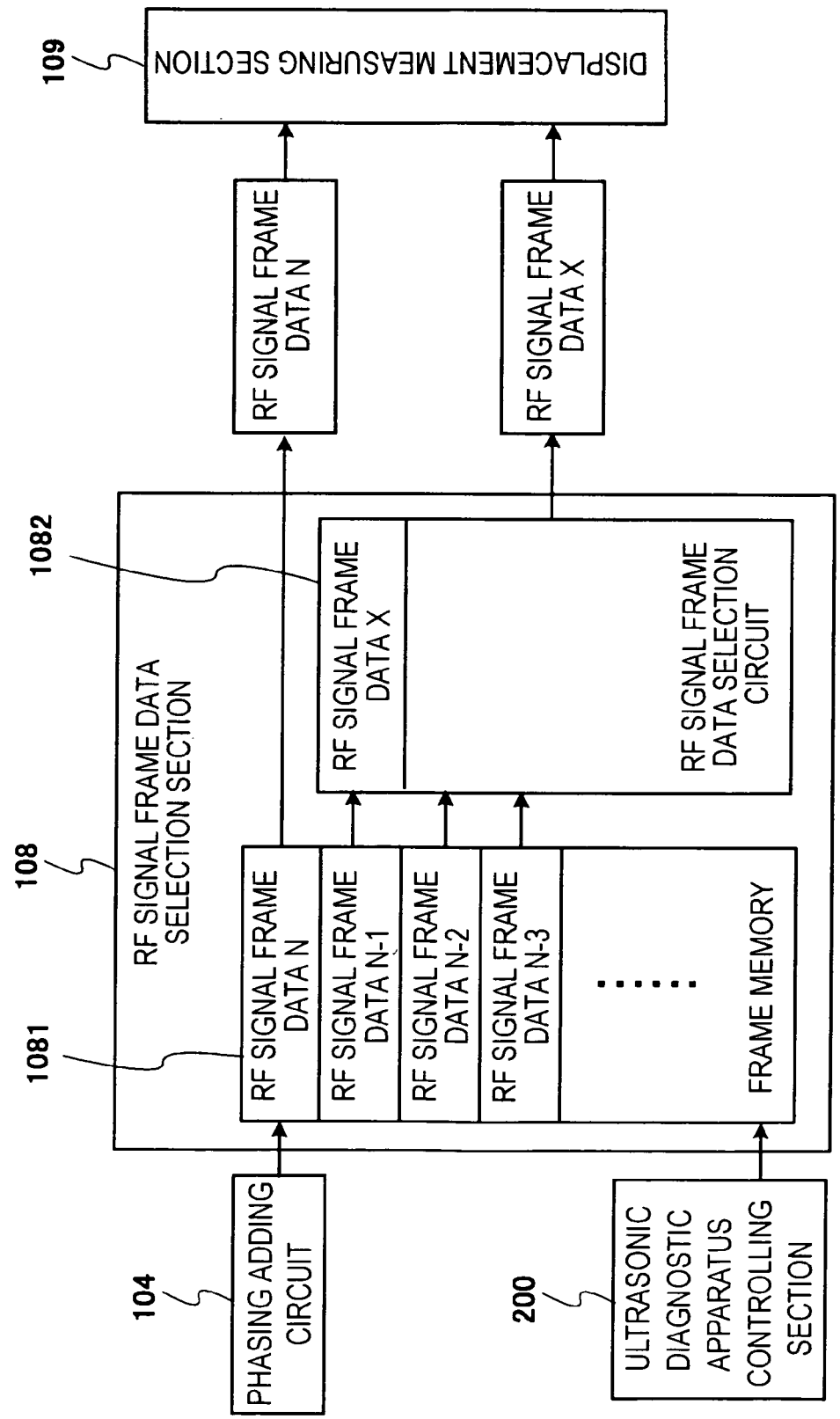
FIG. 13 is a diagram illustrating an embodiment of RF signal frame data selecting section in the ultrasonic diagnostic apparatus of FIG. 1.

The operation of RF signal frame data selecting section 108 related to the present invention will now be described referring to FIG. 13. FIG. 13 is a diagram illustrating one embodiment of the RF signal frame data arbitrarily selecting section in FIG. 1. RF signal frame data selecting section 108 is for selecting the number of frames to be retroactive as one RF signal frame data to be the reference of displacement measurement (number of frame intervals between the present frame data). In other words, RF signal frame data selecting section 108 sequentially acquires RF signal frame data being continuously outputted with time from phasing adding circuit 104 with a frame rate of the ultrasonic diagnostic apparatus, to frame memory 1081 being installed in RF signal frame data selecting section 108. RF signal frame data selecting section 108 sets RF signal frame data being presently acquired in frame memory 1081, as RF signal frame data N. RF signal frame data selecting section 108 selects one RF signal frame data out of past RF signal frame data N-1, N-2, N-3, ..., N-M according to the control command from controlling section 200 in the ultrasonic diagnostic apparatus, and stores it temporarily to RF signal frame data selecting circuit 1082 as RF signal frame data X. RF signal frame data selecting section 108 outputs the newest RF signal frame data N being stored in frame memory 1081 and RF signal frame data X being stored in RF signal frame data selecting circuit 1082 to displacement measuring section 109 in parallel.

Namely RF signal frame data selecting section 108 can arbitrarily select as the past RF signal frame data X which configures one set of RF signal frame data for outputting to displacement measuring section 109 not only RF signal frame data N-1 being temporally adjoining to the present RF signal frame data N, but also RF signal frame data N-M of which M frame (M=1,2,3,...) is thinned. Additionally, the thinned out frame interval number M(M=1, 2, 3, ...) can be arbitrarily set or changed via the user interface of the ultrasonic diagnostic apparatus.

Figure 14:
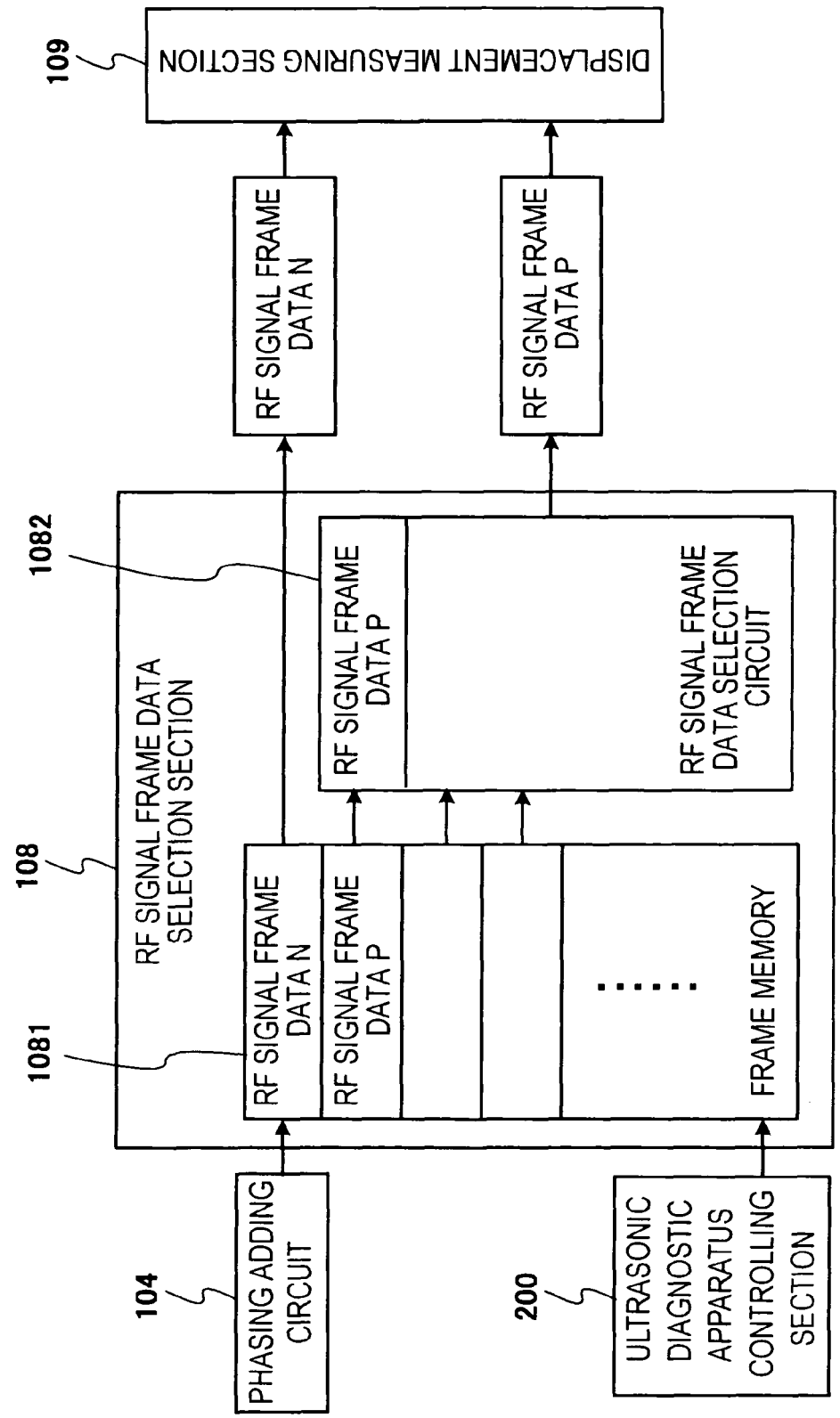
FIG. 14 is a diagram illustrating another embodiment of RF signal frame data selecting section in the ultrasonic diagnostic apparatus of FIG. 1.

FIG. 14 is a diagram illustrating another embodiment of the RF signal frame data selecting section in FIG. 1. RF signal frame data selecting section 108 in FIG. 14 acquires RF signal frame data P being obtained in one time phase P in the past to frame memory 1081 according to the control command from controlling section 200 in the ultrasonic diagnostic apparatus.

RF signal frame data selecting circuit 1082 consistently refers to RF signal frame data P being acquired in frame memory 1081 without updating, as the past RF signal frame data in arbitrary time phase. Thus to displacement measuring section 109, a set of RF signal frame data configured by presently acquired RF signal frame data N and RF signal frame data P is brought in. The setting for whether to apply the feature as seen in FIG. 14 or for the timing to obtain RF signal frame data P upon applying the feature, can be switched, set or changed arbitrarily via the user interface in the ultrasonic diagnostic apparatus.

In the case of limiting the interval of present and past RF signal frame data N and P which configure a set of RF signal frame data, there are occasions that the pressurization quantity or depressurization quantity given in the time intervals between the RF signal frame data which configure a set of the plural RF signal frame data being obtained during a series of pressurizing or depressurizing operation processes are not capable of sufficiently reaching the pressurization or depressurization quantity suited for projecting the elastic image data (generally about 1%). At the same time, by configuring RF signal frame data selecting section as illustrated in FIG. 13 and FIG. 14, it is possible to enlarge the frame intervals between present and past RF signal frame data sufficiently to lead to appropriate projection of the elastic images by the elastic frame data. This is especially useful under conditions wherein the speed of pressurization or depressurization cannot be high enough for the ultrasound examination during the process of sequential pressurization or depressurization operation due to physical restrictions caused by the body frame of the subject.

The invention claimed is:

1. An ultrasonic diagnostic apparatus comprising:
a displacement measuring section for transmitting ultrasonic waves from a probe to an object to be examined, receiving the reflected echo signals corresponding to the transmitted ultrasonic waves, and measuring displacement of organism tissues of the object based on the reflected echo signals;
a tomographic image constructing section for constructing B-mode tomographic image from the reflected echo signals;
an elastic image constructing section for constructing elastic images by obtaining distortion or elastic modulus from said displacement;
a display section for displaying a superposed translucence color image of the elastic image, indicating distribution of hardness of the tissues on the B-mode tomographic image; and
a scoring section configured to classify the elastic image into score corresponding to the distorted state or elastic state, the score being based on whether area of a hard portion of the superposed translucence color image of the elastic image reaches circumference of the low echo region of the B-mode tomographic image, within low echo region of the B-mode tomographic image.

2. The ultrasonic diagnostic apparatus according to claim 1, wherein the area is determined by number of pixels on the elastic image.

3. The ultrasonic diagnostic apparatus according to claim 1 further comprising a region setting means for setting regions on the tomographic or elastic images.

4. The ultrasonic diagnostic apparatus according to claim 3, wherein the region setting means sets the regions by arranging a low echo region on the tomographic images as a first region and a region for the hard portion on the elastic images as a second region, and the scoring section classifies the elastic image into the score corresponding to the distorted state or elastic state according to a proportion between the first region and the second region.

5. The ultrasonic diagnostic apparatus according to claim 3, wherein the region setting means obtains the regions by region growing means for extracting the regions by luminance of the elastic images or the tomographic images, or by edge detection means.

6. The ultrasonic diagnostic apparatus according to claim 5, wherein the region growing means sets a position within the region as a source point, and extracts the region that fits within a threshold value of a difference of luminance set in advance and that adjoins the set source point.

7. The ultrasonic diagnostic apparatus according to claim 3, wherein the region setting means inputs an outline on the tomographic images or the elastic images, and obtains the regions on the basis of the outline information.

8. The ultrasonic diagnostic apparatus according to claim 4, wherein the scoring section sets a plurality of regions of interest, and classifies the elastic image into the score corresponding to the distorted state or elastic state based on an occupancy rate of the hard portion in a plurality of region of interest.

9. The ultrasonic diagnostic apparatus according to claim 4, wherein the scoring section sets a region of interest in the center of the low echo region, and classifies the elastic image into the score corresponding to the distorted state or elastic state based on an occupancy rate of the hard portion in the elastic image.

10. The ultrasonic diagnostic apparatus according to claim 1 further comprising a pressure setting means for setting pressure value that compresses the object, wherein the scoring section classifies the elastic image into the score corresponding to the distorted state or elastic state upon reaching the set pressure value.

11. The ultrasonic diagnostic apparatus according to claim 1, wherein the scoring section classifies the elastic image into the score corresponding to the distorted state or elastic state amongst a plurality of candidate states based on said hard portion within said region.

12. The ultrasonic diagnostic apparatus according to claim 1, wherein a scoring input column is arranged on a screen of the display section, and scores are inputted in the scoring input column using an input means.

13. The ultrasonic diagnostic apparatus according to claim 1 further comprising a frame data selecting section for selecting a set of frame data of reflected echo signals for outputting to the displacement measuring section, wherein the elastic images are constructed based on a set of selected frame data.

14. The ultrasonic diagnostic apparatus according to claim 13, wherein the frame data selecting section arbitrarily selects frame intervals of a set of frame data, the elastic images are constructed based on a set of selected frame data.

15. The ultrasonic diagnostic apparatus according to claim 13, wherein the frame data selecting section selects the frame data from a set of adjoining frames.

16. The ultrasonic diagnostic apparatus according to claim 1, wherein the scoring section classifies the elastic image into the score corresponding to the distorted state or elastic state based on stress signals of the elastic image.

17. The ultrasonic diagnostic apparatus according to claim 1, wherein the scoring section classifies the elastic image into the score corresponding to the distorted state or elastic state based on variance of a region on the elastic image caused by gradual compression.

18. A diagnostic method for an ultrasonic diagnostic apparatus, said method comprising:

transmitting ultrasonic waves from a probe of the ultrasonic diagnostic apparatus to an object to be examined, receiving reflected echo signals corresponding to the transmitted ultrasonic waves, and measuring, by a displacement measuring section of the ultrasonic diagnostic apparatus, displacement of organism tissues of the object based on the reflected echo signals;

constructing, by a tomographic image constructing section of the ultrasonic diagnostic apparatus, B-mode tomographic image from the reflected echo signals;

constructing, by an elastic image constructing section of the ultrasonic diagnostic apparatus, elastic images by obtaining distortion or elastic modulus from said displacement;

displaying, by a display section of the ultrasonic diagnostic apparatus, a superposed translucence color image of the elastic image, indicating distribution of hardness of the tissues on the B-mode tomographic image; and classifying, by a scoring section of the ultrasonic diagnostic apparatus, the elastic image into score corresponding to the distorted state or elastic state, based on whether area of a hard portion of the superposed translucence color image of the elastic image reaches circumference of the low echo region of the B-mode tomographic image, within low echo region of the B-mode tomographic image.

19. The ultrasonic diagnostic apparatus according to claim 1, wherein the scoring section determines an area of the low echo region in the B-mode tomographic image, determines the area of the hard portion in the elastic image, determines a ratio of the area of the hard portion to the area of the low echo region, and classifies the elastic image into the score based on the ratio of the area of the hard portion to the area of the low echo region.

20. The ultrasonic diagnostic apparatus according to claim 1, wherein the scoring section detects the low echo region in the B-mode tomographic image, determines an area of the low echo region, determines the area of the hard portion in the elastic image, determines a ratio of the area of the hard portion to the area of the low echo region, and classifies the elastic image into the score based on the ratio of the area of the hard portion to the area of the low echo region.

* * * * *